United States Patent [19]

Cunkle et al.

[11] Patent Number: 5,204,474
[45] Date of Patent: Apr. 20, 1993

[54] 2,6-DIARYLPIPERIDIN-1-YL SUBSTITUTED 2-BUTENE STABILIZERS

[75] Inventors: Glen T. Cunkle, Stamford, Conn.; Joseph E. Babiarz, Amawalk, N.Y.

[73] Assignee: Ciba-Geigy Corporation, Ardsley, N.Y.

[21] Appl. No.: 709,688

[22] Filed: Jun. 3, 1991

[51] Int. Cl.⁵ ............... C07D 401/06; C07D 498/10; C07D 513/10; C07D 515/10

[52] U.S. Cl. .................. 546/193; 546/16; 546/230; 546/232; 546/234; 546/235; 544/6; 544/70; 544/230

[58] Field of Search ............ 546/193, 230, 232, 234, 546/235, 16; 544/6, 70, 230

[56] References Cited

U.S. PATENT DOCUMENTS

3,932,564  1/1976  Markhart et al. ............ 260/899

FOREIGN PATENT DOCUMENTS

0249145 12/1987 European Pat. Off. .
1438482  6/1976 United Kingdom .
8101706  6/1981 World Int. Prop. O. ......... 546/223

OTHER PUBLICATIONS

V. Baliah et al., Indian J. Chem. 16B, 1065 (1978).
C.A. vol. 80, 120713h (1974).
C.A. vol. 76, 14281y (1972).
C.A. vol. 77, 877256 (1972).

Primary Examiner—C. Warren Ivy
Assistant Examiner—Celia Chang
Attorney, Agent, or Firm—Luther A. R. Hall

[57] ABSTRACT

2,6-Diarylpiperidin-1-yl substituted 2-butene stabilizers of the formula I or II $$T-CH_2-CH=CH-CH_2-T \quad (I)$$

$$T-CH_2-CH=CH-CH_2-N(E_1)(E_2) \quad (II)$$

where T is a 2,6-diarylpiperidin-1-yl moiety and $E_1$ and $E_2$ are independently alkyl, cycloalkyl, aralkyl or aryl, are effective in stabilizing organic materials against the deleterious effects of oxygen, heat and actinic radiation.

6 Claims, No Drawings

2,6-DIARYLPIPERIDIN-1-YL SUBSTITUTED 2-BUTENE STABILIZERS

The present invention pertains to novel 2,6-diaryl-piperidin-1-yl substituted 2-butene compounds and their use as stabilizers for various organic materials subject to the deleterious effects of oxygen, heat or actinic radiation. The instant compounds provide good retention of polymer physical properties during long-term thermooxidative stress.

BACKGROUND OF THE INVENTION

Substituted 1,4-diamino-2-butene compounds are known in the art where the substitution on the N-atoms is alkyl or benzyl, but their use as stabilizers is not disclosed or suggested.

When such substitution is aryl, British Patent No. 1,438,482 generally describes N,N,N',N'-tetraaryl-2-butene-1,4-diamine as stabilizers for lubricant compositions, but does not specifically disclose such compounds. British 1,438,482 does not suggest that such aryl substituted compounds can provide effective antioxidant protection to synthetic polymers.

The compounds of this invention and their use as stabilizers for organic materials subject to degradation by oxygen, heat or light are not disclosed or suggested in the prior art.

OBJECTS OF THE INVENTION

One object of this invention is to provide new substituted 2-butene compounds which are useful stabilizers for various substrates.

Another object of the invention is to provide synthetic polymer compositions stabilized against the deleterious effects of oxygen, heat and light by incorporating therein an effective amount of an instant compound.

DETAILED DISCLOSURE

The instant invention pertains to novel compounds of formula I or II $$T-CH_2-CH=CH-CH_2-T \quad (I)$$

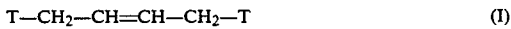

$$T-CH_2-CH=CH-CH_2-N(E_1)(E_2) \quad (II)$$

wherein $E_1$ and $E_2$ are independently alkyl of 1 to 30 carbon atoms, said alkyl terminated with cycloalkyl of 5 to 12 carbon atoms, said alkyl terminated with —CN, —OR$_{16}$, —NR$_{17}$R$_{18}$, —SR$_{19}$, —COOR$_{20}$ or —CONR$_{21}$R$_{22}$, where R$_{16}$, R$_{17}$, R$_{18}$, R$_{19}$ and R$_{20}$ are independently alkyl of 1 to 20 carbon atoms or alkenyl of 3 to 18 carbon atoms, and R$_{21}$ and R$_{22}$ are independently hydrogen or the same meaning as R$_{16}$; or said alkyl interrupted by one or more —O—, —S—, —SO—, —SO$_2$—, —CO—, —COO—, —OCO—, —CONR$_{23}$—, —NR$_{23}$CO— or —NR$_{24}$— where R$_{23}$ and R$_{24}$ have the same meaning as R$_{21}$; alkenyl of 3 to 20 carbon atoms; aralkyl of 7 to 15 carbon atoms or said aralkyl substituted on the aryl ring by one to three groups selected from alkyl of 1 to 12 carbon atoms, —CN, —NO$_2$, halogen, —OR$_{16}$, —NR$_{17}$R$_{18}$, —SR$_{19}$, —COOR$_{20}$ or —CONR$_{21}$R$_{22}$, or aryl of 6 to 10 carbon atoms or said aryl substituted by one to three substituents selected from the group consisting of alkyl of 1 to 20 carbon atoms, cycloalkyl of 5 to 12 carbon atoms and aralkyl of 7 to 15 carbon atoms;

T is a group of formula III, IV, V or VI

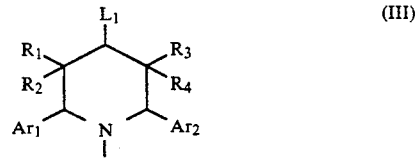

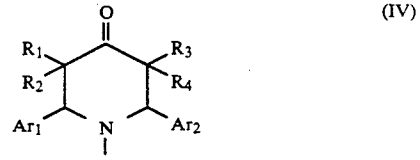

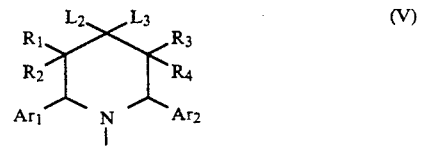

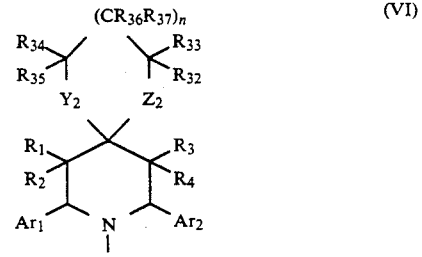

where Ar$_1$ and Ar$_2$ are independently aryl of 6 to 10 carbon atoms; or said aryl substituted by one to three substituents selected from the group consisting of alkyl of 1 to 20 carbon atoms, cycloalkyl of 5 to 12 carbon atoms, phenylalkyl of 7 to 15 carbon atoms, —COOG$_1$ where G$_1$ is hydrogen or alkyl of 1 to 20 carbon atoms, —COG$_2$ where G$_2$ is alkyl of 1 to 20 carbon atoms, —NR$_5$R$_6$ where R$_5$ and R$_6$ are independently hydrogen or alkyl of 1 to 20 carbon atoms, —SG$_3$ where G$_3$ is aryl of 6 to 10 carbon atoms or alkyl of 1 to 20 carbon atoms, —OH, —OCH$_3$, —CN, —CF$_3$, —NO$_2$, —F, —Cl, —Br or —I;

R$_1$, R$_2$, R$_3$ and R$_4$ are independently hydrogen; a linear or branched alkyl of 1 to 30 carbon atoms; said alkyl terminated with —OR$_7$, —NR$_8$R$_9$, —SR$_{10}$, —COOR$_{11}$ or —CONR$_{12}$R$_{13}$, where R$_7$, R$_8$, R$_9$, R$_{10}$ and R$_{11}$ are independently hydrogen, alkyl of 1 to 20 carbon atoms or alkenyl of 3 to 18 carbon atoms, and R$_{12}$ and R$_{13}$ are independently hydrogen or the same meaning as R$_{11}$; or said alkyl interrupted by one or more —O—, —S—, —SO—, —SO$_2$—, —CO—, —COO—, —OCO—, —CONR$_{14}$—, —NR$_{14}$CO— or —NR$_{15}$— where R$_{14}$ and R$_{15}$ have the same meaning as R$_{12}$; alkenyl of 3 to 20 carbon atoms; or aryl of 6 to 10 carbon atoms;

L$_1$ is hydrogen, —OR$_{25}$ where R$_{25}$ is hydrogen or alkyl of 1 to 30 carbon atoms, —NR$_{26}$R$_{27}$, —OCOR$_{28}$, —NCOR$_{29}$ where R$_{26}$, R$_{27}$, R$_{28}$ and R$_{29}$ have the same meaning as R$_{25}$;

L$_2$ and L$_3$ are independently —Y$_1$—R$_{30}$ or —Z$_1$—R$_{31}$ where Y$_1$ and Z$_1$ are independently —O—, —S— or —NR$_{26}$—, and R$_{30}$ and R$_{31}$ are hydrogen or alkyl of 1 to 30 carbon atoms; and n is 0 or 1, Y$_2$ and Z$_2$ are independently —O—, —S— or —NR$_{26}$—, and R$_{32}$, R$_{33}$, R$_{34}$, R$_{35}$, R$_{36}$ and R$_{37}$ are independently hydrogen or alkyl of 1 to 30 carbon atoms.

Preferably Ar$_1$ and Ar$_2$ are phenyl.

Preferably R$_1$, R$_2$, R$_3$ and R$_4$ are independently hydrogen or methyl, most preferably hydrogen.

Preferably E$_1$ and E$_2$ are each benzyl.

Preferably T is a structure of formula III where L$_1$ is hydrogen.

The instant invention also pertains to stabilized compositions comprising (a) an organic material subject to oxidative, thermal or actinic degradation, and (b) an effective stabilizing amount of a compound of formula I or II as defined above.

The preparation of 2,6-diphenylpiperidine is described by V. Balaih et al., Indian J. Chem., 16B, 1065 (1978).

The compounds of formula I and formula II are conveniently prepared by reacting an appropriate secondary amine such as 2,6-diphenylpiperidine with 1,4-but-2-enediol diacetate in the presence of a catalyst such as tetrakis(triphenylphosphine)palladium(0) in an organic solvent such as tetrahydrofuran.

The starting materials for making the instant compounds are largely items of commerce.

When any of Ar$_1$, Ar$_2$, R$_1$ to R$_{37}$, E$_1$, E$_2$, L$_1$, L$_2$, or G$_1$ to G$_3$ is alkyl, such alkyl groups are, for example, methyl, ethyl, isopropyl, n-butyl, tert-butyl, tert-amyl, 2-ethylhexyl, n-octyl, n-undecyl, lauryl, n-heptadecyl, n-octadecyl, eicosyl and tricontyl; when said radicals are cycloalkyl, they are, for example, cyclopentyl, cyclohexyl, cyclooctyl and cyclododecyl; when said radicals are aralkyl, they are, for example, benzyl, phenethyl, a-methylbenzyl, a,a-dimethylbenzyl and 1-naphthylmethyl; when said radicals are aryl, they are, for example, phenyl, naphthyl or when substituted by alkyl are, for example, tolyl and xylyl; and when said radicals are alkyl interrupted by —O—, they are, for example, 3-oxaamyl and 3,6-dioxaoctyl.

The compositions where component (a) is a synthetic polymer are especially a part of this invention, most particularly when the synthetic polymer is a polyolefin such as polypropylene or is an elastomer such as dynamically crosslinked polypropylene/nitrile rubber.

The instant compounds are effective stabilizers for synthetic polymers subject to the deleterious effects of heat and/or oxygen especially during processing at elevated temperatures.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene-/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated monophenols, for example,
2,6-di-tert-butyl-4-methylphenol
2-tert.butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-($\alpha$-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-($\alpha$-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-($\alpha$-methylbenzyl)-4-nonylphenol]
2,2'-methylene-bis-[6-($\alpha,\alpha$-dimethylbenzyl)-4-nonylphenol]
2,2'-methylene-bis-(4,6-di-tert-butylphenol)

2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodeithylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodeithylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example,
diphenylamine, N-phenyl-1-naphthylamine, N-(4-tert-octylphenyl)-1-naphthylamine,
4,4'-di-tert-octyl-diphenylamine, reaction product of N-phenylbenzylamine and
2,4,4-trimethylpentene, reaction product of diphenylamine and 2,4,4-trimethylpentene, reaction
product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3', 5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetra-methylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), bis(1-octyloxy-2,2,6,6-tetramethylpiperidin-4-yl) sebacate.

2.7. Oxalic acid diamides, for example, 4,4'-di-octyloxy-oxanilide, 2,2'-di-octyloxy-5,5'-di-tert-butyloxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)-phenyl]-6-(2,4-dimethylphenyl)-s-triazine; 2,4-bis[2-hydroxy-4-(2-hydroxyethoxy)-phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)-benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylene-bis-(amino-2,2,6,6-tetra-methylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino- 2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]-undecane) diethyl] 1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]-undecane)diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one) and bis(1-octyloxy-2,2,6,6-tetramethylpiperidin-4-yl) sebacate.

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperdine and succinic acid, the polycondensation product of 2,4-dichloro-6-tert-octylamino-s-triazine and 4,4'-hexamethylenebis-(amino-2,2,6,6-tetramethylpiperidine), N,N',N'',N'''-tetrakis[(4,6-bis(butyl-(2,2,6,6-tetramethyl-piperidin-4-yl)amino)-s-triazine-2-yl]-1,10-diamino-4,7-diazadecane or bis(1-octyloxy-2,2,6,6-tetramethylpiperidin-4-yl) sebacate.

The following examples are presented for the purpose of illustration only and are not to be construed as limiting the nature or scope of the instant invention in any manner whatsoever.

EXAMPLE 1

1,4-Bis(2,6-diphenylpiperidin-1-yl)-2-butene

A solution of 2,6-diphenylpiperidine [3.0 g, 12.6 mmol; prepared by the method of V. Baliah et al., Indian J. Chem., 16B, 1965 (1978)] and 1,4-but-2-enediol diacetate (1.1 g, 6.3 mmol) in tetrahydrofuran (20 ml, THF) is treated with tetrakis(triphenylphosphine)palladium (0) (0.65 g, 0.6 mmol) and stirred at room temperature overnight. The reaction mixture is concentrated in vacuo to a solid that is redissolved in THF (100 ml) and treated with 20% aqueous sodium hydroxide (25 ml). The mixture is stirred for one hour, concentrated, and extracted with diethyl ether. The ether extracts are dried and concentrated giving an orange solid which is purified by crystallization from methanol to yield 2.02 g (61%) of the title compound as a white solid melting at 197°-200° C.

Analysis: Calcd for $C_{38}H_{42}N_2$: C, 86.6; H, 8.0; N, 5.3. Found: C, 86.7; H, 8.0; N, 5.2.

EXAMPLE 2

1-(2,6-Diphenylpiperidin-1-yl)-4-dibenzylamino-2-butene

A solution of dibenzylamine (40 g, 0.20 mol) and 1,4-but-2-enediol diacetate (105 g, 0.61 mol) in THF (150 ml) is treated with tetrakis(triphenylphosphine)palladium (0) (1 g, 0.9 mmol) and stirred at room temperature overnight. The reaction mixture is concentrated in vacuo and the excess 1,4-but-2-enediol is removed by bulb-to-bulb distillation (80°-90° C., 1 mm). The residue is purified by eluting through a short plug of silica gel (1:1, ethyl acetate:hexanes). 59.2 g (95%) of 1-acetoxy-4-dibenzylamino-2-butene is obtained.

A solution of 1-acetoxy-4-dibenzylamino-2-butene (3.0 g, 9.8 mmol) and 2,6-diphenylpiperidine (2.3 g, 9.8 mmol) in THF (25 ml) is treated with tetrakis(triphenylphosphine)palladium (0) (0.5 g, 0.45 mmol) and stirred at room temperature overnight. The reaction mixture is concentrated in vacuo. The residue is redissolved in THF (100 ml) and treated with 20% aqueous sodium hydroxide (25 ml). The mixture is stirred for one hour, concentrated, and extracted with diethyl ether. The ether extracts are dried and concentrated to give an orange oil which is purified by chromatography (silica gel; 5% ethyl acetate in hexanes) to give the title compound in a yield of 2.8 g (59%) as a clear oil. MS m/z 486 (M+)

EXAMPLE 3

Process Stabilization of Dynamically Crosslinked Polypropylene/Nitrile Rubber

To a Brabender Plasticorder heated to 190° C. is added 55 grams of dynamically corsslinked polypropylene/nitrile rubber (GEOLAST, Monsanto). The polymer is mixed under nitrogen for 3 minutes at 30 rpm and then 2.2 grams (4% by weight of the resin blend) of the test compound is added under nitrogen and mixed into the resin blend at 90 rpm for 7 minutes. The test sample is then removed from the Brabender and flattened in a cold press.

The test sample is then compression molded into plaques (4"×4"×60 mils; 10.16 cm×10.16 cm×1.524 mm) at 200° C. for 4 minutes at 2000 psi (140 Kg/cm$^2$) and then 4 minutes at 50,000 psi (3500 Kg/cm$^2$).

The plaques are then cut into tensile bars and oven aged in a forced draft oven at 135° C. for 7 days. The aged samples are tested for % retention of elongation according to ASTM The % elongation of triplicate bars are measured before and after oven aging. The greater the % retention of the % elongation, the more effective is the stabilizer compound.

The instant compounds of Examples 1 and 2 provide the GEOLAST resin with effective stabilization against thermal oxidative degradation.

What is claimed is:

1. A compound of formula I $$T-CH_2-CH=CH-CH_2-T \qquad (I)$$

wherein

T is a group of formula III, IV, V or VI

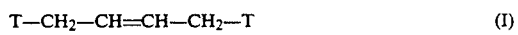

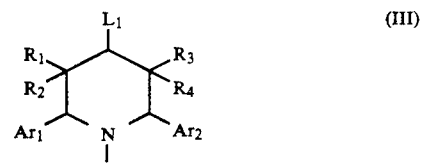
(III)

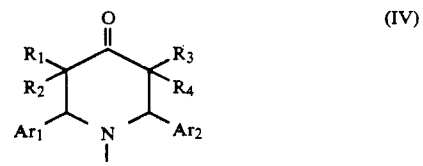
(IV)

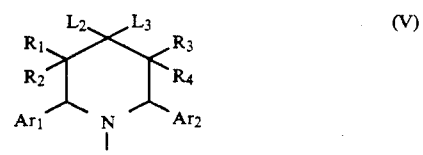
(V)

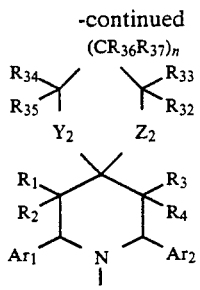

where $Ar_1$ and $Ar_2$ are independently carbocyclic aryl of 6 to 10 carbon atoms; or said aryl substituted by one to three substituents selected from the group consisting of alkyl of 1 to 20 carbon atoms, cycloalkyl of 5 to 12 carbon atoms, phenylalkyl of 7 to 15 carbon atoms, $-COOG_1$ where $G_1$ is hydrogen or alkyl of 1 to 20 carbon atoms, $-COG_2$ where $G_2$ is alkyl of 1 to 20 carbon atoms, $-NR_5R_6$ where $R_5$ and $R_6$ are independently hydrogen or alkyl of 1 to 20 carbon atoms, $-SG_3$ where $G_3$ is carbocyclic aryl of 6 to 10 carbon atoms or alkyl of 1 to 20 carbon atoms, $-OH$, $-OCH_3$, $-CN$, $-CF_3$, $-NO_2$, $-F$, $-Cl$, $-Br$ or $-I$;

$R_1$, $R_2$, $R_3$ and $R_4$ are independently hydrogen; a linear or branched alkyl of 1 to 30 carbon atoms; said alkyl terminated with $-OR_7$, $-NR_8R_9$, $-SR_{10}$, $-COOR_{11}$ or $-CONR_{12}R_{13}$, where $R_7$, $R_8$, $R_9$, $R_{10}$ and $R_{11}$ are independently hydrogen, alkyl of 1 to 20 carbon atoms or alkenyl of 3 to 18 carbon atoms, and $R_{12}$ and $R_{13}$ are independently hydrogen or the same meaning as $R_{11}$; or said alkyl interrupted by one or two $-O-$, $-S-$, $-SO-$, $-SO_2-$, $-CO-$, $-COO-$, $-OCO-$, $-CONR_{14}-$, $-NR_{14}CO-$ or $-NR_{15}-$ where $R_{14}$ and $R_{15}$ have the same meaning as $R_{12}$; alkenyl of 3 to 20 carbon atoms; or carbocyclic aryl of 6 to 10 carbon atoms;

$L_1$ is hydrogen, $-OR_{25}$ where $R_{25}$ is hydrogen or alkyl of 1 to 30 carbon atoms, $-NR_{26}R_{27}$, $-OCOR_{28}$, $-NCOR_{29}$ where $R_{26}$, $R_{27}$, $R_{28}$ and $R_{29}$ have the same meaning as $R_{25}$;

$L_2$ and $L_3$ are independently $-Y_1-R_{30}$ or $-Z_1-R_{31}$ where $Y_1$ and $Z_1$ are independently $-O-$, $-S-$ or $-NR_{26}-$, and $R_{30}$ and $R_{31}$ are hydrogen or alkyl of 1 to 30 carbon atoms; and n is 0 or 1, $Y_2$ and $Z_2$ are independently $-O-$, $-S-$ or $-NR_{26}-$, and $R_{32}$, $R_{33}$, $R_{34}$, $R_{35}$, $R_{36}$ and $R_{37}$ are independently hydrogen or alkyl of 1 to 30 carbon atoms.

2. A compound according to claim 1 wherein $Ar_1$ and $Ar_2$ are phenyl.

3. A compound according to claim 1 wherein $R_1$, $R_2$, $R_3$ and $R_4$ are independently hydrogen or methyl.

4. A compound according to claim 3 wherein $R_1$, $R_2$, $R_3$ and $R_4$ are each hydrogen.

5. A compound according to claim 1 wherein T is a structure of formula III where $L_1$ is hydrogen.

6. The compound according to claim 1 which is 1,4-bis(2,6-diphenylpiperidin-1yl)-2-butene.

* * * * *